(12) United States Patent
Singh et al.

(10) Patent No.: US 10,340,866 B2
(45) Date of Patent: Jul. 2, 2019

(54) SINGLE-ENDED TRANS-IMPEDANCE AMPLIFIER (TIA) FOR ULTRASOUND DEVICE

(71) Applicant: Butterfly Network, Inc., Guilford, CT (US)

(72) Inventors: Amandeep Singh, Jersey City, NJ (US); Kailiang Chen, Branford, CT (US); Tyler S. Ralston, Clinton, CT (US)

(73) Assignee: Butterfly Network, Inc., Guilford, CT (US)

( * ) Notice: Subject to any disclaimer, the term of this patent is extended or adjusted under 35 U.S.C. 154(b) by 0 days.

(21) Appl. No.: 16/244,934

(22) Filed: Jan. 10, 2019

(65) Prior Publication Data

US 2019/0149109 A1    May 16, 2019

Related U.S. Application Data

(63) Continuation of application No. 16/011,742, filed on Jun. 19, 2018.

(Continued)

(51) Int. Cl.
*H03F 3/45* (2006.01)
*H03M 1/38* (2006.01)
(Continued)

(52) U.S. Cl.
CPC ..... *H03F 3/45179* (2013.01); *G01N 29/2406* (2013.01); *G01N 29/4463* (2013.01);
(Continued)

(58) Field of Classification Search
CPC ....... H03F 3/45179; H03F 2203/45116; H03F 2200/129; H03F 2203/45524;
(Continued)

(56) References Cited

U.S. PATENT DOCUMENTS 4,829,491 A   5/1989  Saugeon et al.
5,844,445 A   12/1998 Takeyari
(Continued)

FOREIGN PATENT DOCUMENTS

CN        103607130 A       2/2014
WO    WO-2018236778 A1 *  12/2018  ........... A61B 8/5207
(Continued)

OTHER PUBLICATIONS

International Search Report and Written Opinion dated Feb. 7, 2017 for Application No. PCT/US2016/064314.
(Continued)

*Primary Examiner* — Daniel Pihulic
(74) *Attorney, Agent, or Firm* — Wolf, Greenfield & Sacks, P.C.

(57) ABSTRACT

An ultrasound circuit comprising a single-ended trans-impedance amplifier (TIA) is described, The TIA is coupled to an ultrasonic transducer to amplify an electrical signal generated by the ultrasonic transducer in response to receiving an ultrasound signal. The TEA is followed by further processing circuitry configured to filter, amplify, and digitize the signal produced by the TIA.

18 Claims, 7 Drawing Sheets

Related U.S. Application Data

(60) Provisional application No. 62/522,606, filed on Jun. 20, 2017.

(51) Int. Cl.
   *G01N 29/24* (2006.01)
   *G01N 29/44* (2006.01)
   *H03M 1/12* (2006.01)

(52) U.S. Cl.
   CPC ........ *H03M 1/124* (2013.01); *H03F 2200/129* (2013.01); *H03F 2203/45116* (2013.01); *H03F 2203/45524* (2013.01); *H03M 1/38* (2013.01)

(58) Field of Classification Search
   CPC .... H03M 1/124; H03M 1/38; G01N 29/4463; G01N 29/2406
   See application file for complete search history.

(56) References Cited

U.S. PATENT DOCUMENTS

| | | |
|---|---|---|
| 6,356,152 B1 | 3/2002 | Jezdic et al. |
| 6,404,281 B1 | 6/2002 | Kobayashi |
| 7,313,053 B2 | 12/2007 | Wodnicki |
| 7,449,958 B1 | 11/2008 | Voo |
| 7,605,660 B1 | 10/2009 | Kobayashi |
| 8,662,395 B2 | 3/2014 | Melandso et al. |
| 8,852,103 B2 | 10/2014 | Rothberg et al. |
| 9,229,097 B2 | 1/2016 | Rothberg et al. |
| 9,473,136 B1 | 10/2016 | Chen et al. |
| 9,492,144 B1 | 11/2016 | Chen et al. |
| 9,521,991 B2 | 12/2016 | Rothberg et al. |
| 9,592,030 B2 | 3/2017 | Rothberg et al. |
| 9,705,518 B2 | 7/2017 | Chen et al. |
| 9,933,516 B2 | 4/2018 | Chen et al. |
| 9,958,537 B2 | 5/2018 | Chen et al. |
| 10,014,871 B2 | 7/2018 | Chen et al. |
| 10,082,488 B2 | 9/2018 | Chen et al. |
| 10,082,565 B2 | 9/2018 | Chen et al. |
| 2007/0001764 A1 | 1/2007 | Huang et al. |
| 2007/0242567 A1 | 10/2007 | Daft et al. |
| 2007/0287923 A1 | 12/2007 | Adkins et al. |
| 2009/0250729 A1 | 10/2009 | Lemmerhirt et al. |
| 2010/0152587 A1 | 6/2010 | Haider et al. |
| 2010/0237807 A1 | 9/2010 | Lemmerhirt |
| 2010/0317972 A1 | 12/2010 | Baumgartner et al. |
| 2011/0130109 A1 | 6/2011 | Ogasawara |
| 2013/0064043 A1 | 3/2013 | Degertekin et al. |
| 2014/0240482 A1 | 8/2014 | Ikeda et al. |
| 2014/0288428 A1 | 9/2014 | Rothberg et al. |
| 2015/0032002 A1 | 1/2015 | Rothberg et al. |
| 2015/0145597 A1 | 5/2015 | Huang et al. |
| 2015/0297193 A1 | 10/2015 | Rothberg et al. |
| 2015/0374335 A1 | 12/2015 | Brown et al. |
| 2016/0228099 A1 | 8/2016 | Matsumura |
| 2017/0143306 A1 | 5/2017 | Rothberg et al. |
| 2017/0160239 A1 | 6/2017 | Chen et al. |
| 2017/0160387 A1 | 6/2017 | Chen et al. |
| 2017/0160388 A1 | 6/2017 | Chen et al. |
| 2017/0163225 A1 | 6/2017 | Chen et al. |
| 2017/0163276 A1 | 6/2017 | Chen et al. |
| 2017/0202541 A1 | 7/2017 | Ralston |
| 2017/0264307 A1 | 9/2017 | Chen et al. |
| 2017/0307739 A1 | 10/2017 | Chen et al. |
| 2018/0070925 A1 | 3/2018 | Chen et al. |
| 2018/0210073 A1 | 7/2018 | Chen et al. |
| 2018/0360426 A1 | 12/2018 | Singh et al. |
| 2018/0361431 A1 | 12/2018 | Singh et al. |
| 2018/0367110 A1 | 12/2018 | Singh et al. |
| 2018/0367111 A1 | 12/2018 | Singh et al. |

FOREIGN PATENT DOCUMENTS

| | | | | |
|---|---|---|---|---|
| WO | WO-2018236779 A1 | * | 12/2018 | ......... H03F 3/45179 |
| WO | WO-2018236786 A1 | * | 12/2018 | ........... B06B 1/0215 |
| WO | WO-2018236799 A1 | * | 12/2018 | ......... H03F 3/45179 |

OTHER PUBLICATIONS

International Preliminary Report on Patentability dated Jun. 14, 2018 in connection with International Application No. PCT/US2016/064314.
International Search Report and Written Opinion dated Aug. 30, 2018 in connection with International Application No. PCT/US2018/038147.
International Search Report and Written Opinion dated Sep. 6, 2018 in connection with International Application No. PCT/US2018/038180.
Taiwanese Office Action dated Jan. 19, 2018 in connection with Taiwanese Application No. 105139662.
Agarwal et al., Single-Chip Solution for Ultrasound Imaging Systems: Initial Results. 2007 IEEE Ultrasonics Symposium. Oct. 1, 2007;1563-6.
Chen et al., Ultrasonic Imaging Front-End Design for CMUT: A 3-Level 30Vpp Pulse-Shaping Pulser with Improved Efficiency and a Noise-Optimized Receiver. IEEE Asian Solid-State Circuits Conference. Nov. 12-14, 2012;173-6.
Cheng et al., An Efficient Electrical Addressing Method Using Through-Wafer Vias for Two-Dimensional Ultrasonic Arrays. 2000 IEEE Ultrasonics Symposium. 2000;2:1179-82.
Cheng et al., CMUT-in-CMOS ultrasonic transducer arrays with on-chip electronics. Transducers 2009. IEEE. Jun. 21, 2009;1222-5.
Cheng et al., Electrical Through-Wafer Interconnects with Sub-PicoFarad Parasitic Capacitance. 2001 Microelectromechan Syst Conf. Aug. 24, 2001;18-21.
Daft et al., A Matrix Transducer Design with Improved Image Quality and Acquisition Rate. 2007 IEEE Ultrasonics Symposium. Oct. 1, 2007;411-5.
Daft et al., Microfabricated Ultrasonic Transducers Monolithically Integrated with High Voltage Electronics. 2004 IEEE Ultrasonics Symposium. Aug. 23, 2004;1:493-6.
Doody et al., Modeling and Characterization of CMOS-Fabricated Capacitive Micromachined Ultrasound Transducers. J Microelectromechan Sys. Feb. 2011;20(1):104-118.
Gurun et al., Front-end CMOS electronics for monolithic integration with CMUT arrays: circuit design and initial experimental results. Proc Ultrason Symp. 2008;390-3.
Khuri-Yakub et al., Miniaturized Ultrasound Imaging Probes Enabled by CMUT Arrays with Integrated Frontend Electronic Circuits. Conf Proc IEEE Eng Med Biol Soc. 2010;1:5987-90. doi:10.1109/IEMBS.2010.5627580. Epub Dec. 6, 2010. 13 pages.
Kim et al., Design and Test of a Fully Controllable 64×128 2-D CMUT Array Integrated with Reconfigurable Frontend ASICs for Volumetric Ultrasound Imaging. IEEE. International Ultrasonics Symposium Proceedings. Oct. 7-10, 2012;77-80. doi: 10.1109/ULTSYM.2012.0019.
Kupnik et al., Wafer-bonded CMUT meets CMOS. MEMS-based Ultrasonic Transducer Arrays including Electronics Integration. 2010 CMOS Emerging Technology Workshop. Whistler, Canada. May 21, 2010. 22 pages.
Orozco, Programmable-Gain Transimpedance Amplifiers Maximize Dynamic Range in Spectroscopy Systems. Analog Dialogue. May 2013;47(05):1-5.

* cited by examiner

SINGLE-ENDED TRANS-IMPEDANCE AMPLIFIER (TIA) FOR ULTRASOUND DEVICE

CROSS-REFERENCE TO RELATED APPLICATIONS

This Application is a Continuation claiming the benefit under 35 U.S.C. § 120 of U.S. application Ser. No. 16/011,742, filed Jun. 19, 2018, and entitled "SINGLE-ENDED TRANS IMPEDANCE AMPLIFIER (TIA) FOR ULTRASOUND DEV1CE," which is hereby incorporated herein by reference in its entirety.

U.S. application Ser. No. 16/011,742 claims the benefit under 35 USC § 119(e) of U.S. Provisional Patent Application Ser. No. 62/522,606, filed Jun. 20, 2017 and entitled "SINGLE-ENDED TRANS-IMPEDANCE AMPLIFIER (TIA) FOR ULTRASOUND DEV1CE," which is hereby incorporated herein by reference in its entirety.

BACKGROUND

Field

The present application relates to ultrasound devices having an amplifier for amplifying received ultrasound signals.

Related Art

Ultrasound probes often include one or more ultrasound sensors which sense ultrasound signals and produce corresponding electrical signals. The electrical signals are processed in the analog or digital domain. Sometimes, ultrasound images are generated from the processed electrical signals.

BRIEF SUMMARY

According to an aspect of the present application, an ultrasound apparatus is provided, comprising an ultrasound sensor and a single-ended trans-impedance amplifier (TIA) coupled to the ultrasound sensor and configured to receive and amplify an output signal from the ultrasound sensor.

According to an aspect of the present application, an ultrasound apparatus is provided, comprising an ultrasonic transducer, and a single-ended trans-impedance amplifier (TIA) having an input terminal coupled to the ultrasonic transducer and configured to receive and amplify an analog electrical signal from the ultrasonic transducer.

According to an aspect of the present application, an ultrasound circuit is provided, comprising an ultrasonic transducer, and a plurality of analog processing stages coupled to an output of the ultrasonic transducer. The plurality of analog processing stages includes one analog processing stage configured to exhibit a greater voltage swing than other analog processing stages of the plurality of analog processing stages.

According to an aspect of the present application, an ultrasound circuit is provided, comprising an ultrasonic transducer, an amplifier having an input terminal coupled to the ultrasonic transducer, and a time gain compensation (TGC) circuit. The amplifier is electrically coupled between the ultrasonic transducer and the TGC circuit. The amplifier is configured to exhibit a first voltage swing and the TGC circuit is configured to exhibit a second voltage swing greater than the first voltage swing.

BRIEF DESCRIPTION OF DRAWINGS

Various aspects and embodiments of the application will be described with reference to the following figures. It should be appreciated that the figures are not necessarily drawn to scale. Items appearing in multiple figures are indicated by the same reference number in all the figures in which they appear.

DETAILED DESCRIPTION

Figure 1:
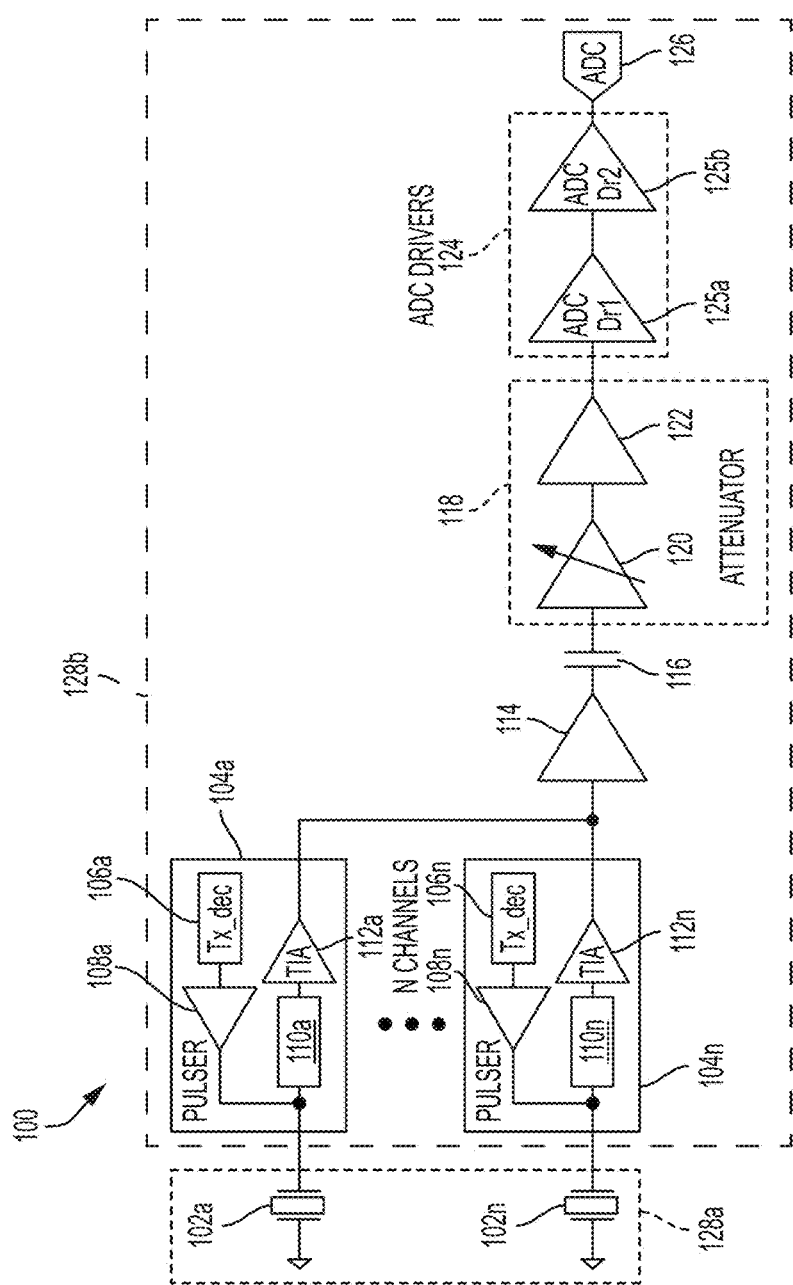
FIG. 1 is a block diagram of an ultrasound device including an amplifier for amplifying an ultrasound signal, according to a non-limiting embodiment of the present application.

Aspects of the present application relate to amplification circuitry for an ultrasound device. An ultrasound device may include one or more ultrasonic transducers configured to receive ultrasound signals and produce electrical output signals. Thus, the ultrasonic transducers may be operated as ultrasound sensors. The ultrasound device may include one or more amplifiers for amplifying the electrical output signals. In some embodiments, the amplifier(s) may be a single-ended trans-impedance amplifier (TIA).

According to an aspect of the present application, analog processing stages (alternatively referred to herein as "blocks" or "components") may follow a single-ended TIA of an ultrasound device. The analog processing stages may perform various analog processing functions, such as filtering an electrical signal produced by the single-ended TIA. In some embodiments, the TIA and all but one of the analog processing stages have a first voltage swing, and a time gain compensation stage representing the last analog processing stage has a second voltage swing greather than the first voltage swing. Such a configuration may facilitate use of a single-ended TIA in the signal chain, which may therefore provide for lower power operation than if a differential or pseudo-differential TIA was implemented. Also, the power of the signal processing chain may be reduced because less power is consumed to maintain linearity through the signal chain.

According to an aspect of the present application, an ultrasound circuit is provided, comprising an ultrasonic transducer, a multi-stage analog processing circuit, and an analog-to-digital converter (ADC). In some embodiments, the multi-stage analog processing circuit includes a plurality of processing stages operating at a first voltage swing and a time gain compensation (TGC) stage operating at a larger voltage swing. The plurality of processing stages operating at the first voltage swing may include a single-ended TIA.

According to an aspect of the present application, a method of processing ultrasound signals is provided. The method comprises generating an electrical signal using an ultrasonic transducer, and amplifying the electrical signal with a single-ended TIA. In some embodiments, multiple single-ended TIAs are provided, and further processing comprises averaging the signals provided by multiple single-ended TIAs and filtering the averaged signal. Amplifying the electrical signal from the ultrasonic transducer, and averaging and filtering the signal(s) from the single-ended TIA may be performed using components providing a first voltage swing. In some embodiments, the method further comprises performing time gain compensation (TGC) on the signals after averaging and filtering, and prior to converting the analog signals to digital signals with an ADC. The TGC may be performed using a TGC stage providing a second voltage swing greater than the voltage swing provided by preceding analog stages.

According to an aspect of the present application, a circuit is provided for processing ultrasound signals. The circuit may include an ultrasonic transducer which produces analog electrical signals in response to receiving an ultrasound signal, analog processing circuitry to process (e.g., amplify, filter, and compensate) the analog signals, and an ADC to convert the analog electrical signals into digital signals. An ADC driver for the ADC may include a super source follower in at least some embodiments.

The aspects and embodiments described above, as well as additional aspects and embodiments, are described further below. These aspects and/or embodiments may be used individually, all together, or in any combination of two or more, as the application is not limited in this respect.

FIG. 1 illustrates a circuit for processing received ultrasound signals, according to a non-limiting embodiment of the present application. The circuit 100 includes N ultrasonic transducers 102a . . . 102n, wherein N is an integer. The ultrasonic transducers are sensors in some embodiments, producing electrical signals representing received ultrasound signals. The ultrasonic transducers may also transmit ultrasound signals in some embodiments. The ultrasonic transducers may be capacitive micromachined ultrasonic transducers (CMUTs) in some embodiments. The ultrasonic transducers may be piezoelectric micromachined ultrasonic transducers (PMUTs) in some embodiments. Alternative types of ultrasonic transducers may be used in other embodiments.

The circuit 100 further comprises N circuitry channels 104a . . . 104n. The circuitry channels may correspond to a respective ultrasonic transducer 102a . . . 102n. For example, there may be eight ultrasonic transducers 102a . . . 102n and eight corresponding circuitry channels 104a . . . 104n. In some embodiments, the number of ultrasonic transducers 102a . . . 102n may be greater than the number of circuitry channels.

The circuitry channels 104a . . . 104n may include transmit circuitry, receive circuitry, or both. The transmit circuitry may include transmit decoders 106a . . . 106n coupled to respective pulsers 108a . . . 108n. The pulsers 108a . . . 108n may control the respective ultrasonic transducers 102a . . . 102n to emit ultrasound signals.

The receive circuitry of the circuitry channels 104a . . . 104n may receive the (analog) electrical signals output from respective ultrasonic transducers 102a . . . 102n. In the illustrated example, each circuitry channel 104a . . . 104n includes a respective receive circuit 110a . . . 110n and an amplifier 112a . . . 112n. The receive circuit 110a . . . 110n may be controlled to activate/deactivate readout of an electrical signal from a given ultrasonic transducer 102a . . . 102n, An example of suitable receive circuits 110a . . . 110n are switches. That is, in one embodiment the receive circuits are controllable switches which are switched during transmit mode to disconnect the ultrasonic transducers from the receive circuitry and during receive mode to connect the ultrasonic transducers to the receive circuitry. Alternatives to a switch may be employed to perform the same function.

The amplifiers 112a . . . 112n may be single-ended TIAs in some embodiments, outputting amplified analog signals. As will be described further below, in some embodiments one or more and in some embodiments all of the amplifiers 112a-112n may include a common source subcircuit and a source follower. The use of single-ended TIAs may facilitate low power operation of the circuit 100 compared to the use of alternative amplifier designs.

The circuit 100 further comprises an averaging circuit 114, which is also referred to herein as a summer or a summing amplifier. In some embodiments, the averaging circuit 114 is a buffer or an amplifier. The averaging circuit 114 may receive output signals from one or more of the amplifiers 112a . . . 112n and may provide an averaged output signal. The averaged output signal may be formed in part by adding or subtracting the signals from the various amplifiers 112a . . . 112n, The averaging circuit 114 may include a variable feedback resistance. The value of the variable feedback resistance may be adjusted dynamically based upon the number of amplifiers 112a . . . 112n from which the averaging circuit receives signals. In some embodiments, the variable resistance may include N resistance settings. That is, the variable resistance may have a number of resistance settings corresponding to the number of circuitry channels 104a . . . 104n. Thus, the average output signal may also be formed in part by application of the selected resistance to the combined signal received at the inputs) of the averaging circuit 114.

The averaging circuit 114 is coupled to an auto-zero block 116, also referred to herein as a "DC block." The auto-zero block 116 may filter the averaged signal provided by the averaging circuit 114, and thus may be considered a filter in at least some embodiments.

The auto-zero block 116 is coupled to a programmable gain amplifier 118 which includes an attenuator 120 and a fixed gain amplifier 122. The programmable gain amplifier 118 may perform time gain compensation (TGC), and thus may alternatively be referred to as a TGC stage or circuit. In performing TGC, the programmable gain amplifier 118 may increase the amplification provided during reception of an ultrasound signal by an ultrasonic transducer, thus compensating for the natural attenuation of the signal which occurs over time.

The programmable gain amplifier 118 is coupled to an ADC 126 via ADC drivers 124. in the illustrated example. the ADC drivers 124 include a first ADC driver 125a and a second ADC driver 125b. The ADC 126 digitizes the signal(s) from the averaging circuit 114.

While FIG. 1 illustrates a number of components as part of a circuit of an ultrasound device, it should be appreciated that the various aspects described herein are not limited to the exact components or configuration of components illustrated. For example, aspects of the present application relate to the amplifiers 112a . . . 112n, and the components illustrated downstream of those amplifiers in circuit 100 are optional in some embodiments.

The components of FIG. 1 may be located on a single substrate or on different substrates. For example, as illustrated, the ultrasonic transducers 102a . . . 102n may be on a first substrate 128a and the remaining illustrated components may be on a second substrate 128b. The first and/or second substrates may be semiconductor substrates, such as silicon substrates. In an alternative embodiment, the components of FIG. 1 may be on a single substrate. For example, the ultrasonic transducers 102a . . . 102n and the illustrated circuitry may be monolithically integrated on the same die (e.g., a semiconductor die, such as silicon). Such integration may be facilitated by using CMUTs as the ultrasonic transducers.

According to an embodiment, the components of FIG. 1 form part of an ultrasound probe. The ultrasound probe may be handheld. In some embodiments, the components of FIG. 1 form part of an ultrasound patch configured to be worn by a patient, or part of an ultrasound pill to be swallowed by a patient.

Figure 2:
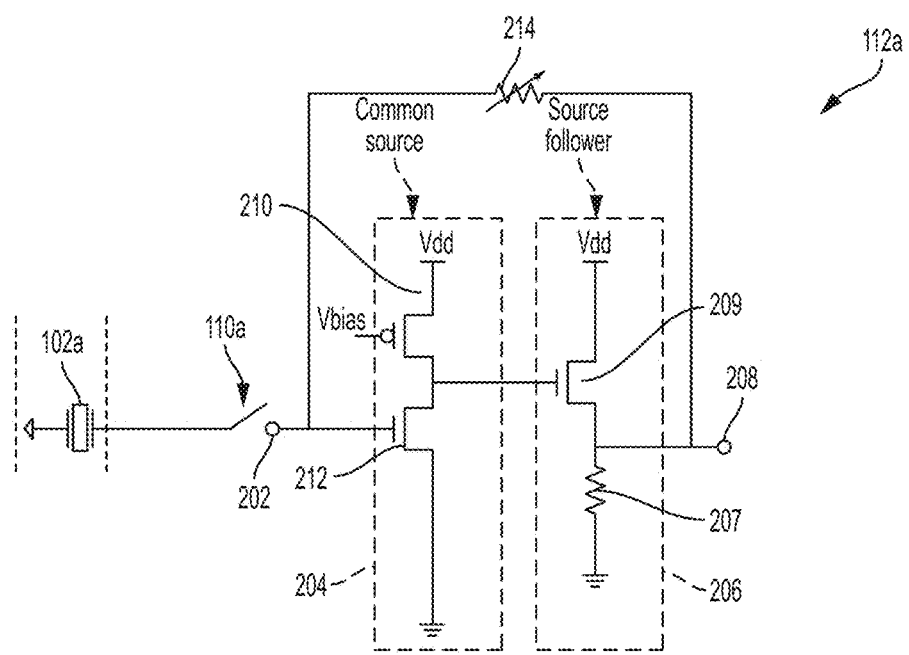
FIG. 2 illustrates the amplifier of FIG. 1 in greater detail, coupled to the ultrasonic transducer of FIG. 1, according to a non-limiting embodiment of the present application.

As previously described, aspects of the present application provide a single-ended TIA for an ultrasound device. FIG. 2 illustrates a non-limiting example of the amplifier 112a of FIG. 1 in greater detail, illustrating a single-ended configuration. The same configuration may be used for the other TIAs 112n of FIG. 1.

The amplifier 112a includes an input terminal 202 coupled to the receive circuit 110a, which is illustrated as a switch in this non-limiting embodiment. The input terminal 202 is therefore coupled to the ultrasonic transducer 102a to receive electrical signals output by the ultrasonic transducer.

The amplifier 112a further comprises a common source subcircuit 204 (referred to herein simply as a "common source"), source follower 206, feedback impedance 214, and output terminal 208. The common source 204 in turn includes a PMOS transistor 210 and NMOS transistor 212 between a power supply rail, Vdd, and ground (GND). The PMOS transistor 210 represents a non-limiting example of a current sourced, with its gate biased by a suitable bias voltage Vbias. Other forms of current sources may alternatively be implemented. The gate of the NMOS transistor 212 may correspond to the input terminal 202, configured to receive the electrical signal output by the ultrasonic transducer 102a. The source follower 206 includes a resistor 207 and NMOS transistor 209, the gate of which is coupled to the drain of NMOS transistor 212 of the common source 204. The resistor 207 is used in the illustrated non-limiting embodiments, but other forms of current sources could alternatively be implemented.

The amplifier 112a also includes a programmable feedback impedance 214, shown in this non-limiting example as a resistor. In some embodiments, the feedback impedance may comprise a resistor in parallel with a capacitor, one or both of which may be variable. The feedback impedance determines the transimpedance gain of the transimpedance amplifier, such that the input current signal may be converted into an output voltage of varying amplitude. The feedback impedance 214 may be programmed before operation, and remains static during operation. Thus, in at least some embodiments the feedback impedance may be considered a programmable static feedback impedance.

The amount of power savings realized from use of a single-ended TIA in an ultrasound signal chain like that illustrated in FIG. 1 may be significant. For example, in the circuit 100, the amplifiers 112a . . . 112n may consume a relatively significant amount of power. In some embodiments, the amplifiers 112a . . . 112n may consume more power than any other components of the circuit 100. Accordingly, reducing the power consumption of the amplifiers 112a . . . 112n may provide a significant reduction in power of the circuit 100. The use of a single-ended TIA may reduce power consumption of the TIA stage by half or more, for a single TIA. Thus, multiplying such power savings by N TIAs may be significant compared to TIA designs which are not single-ended.

Figure 5:
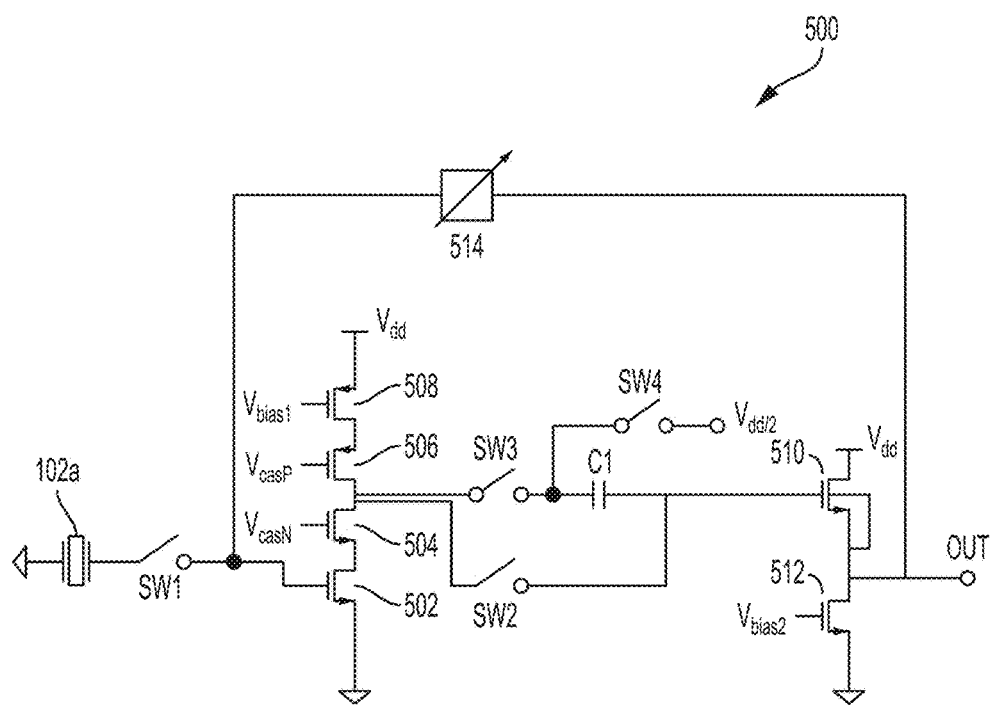
FIG. 5 illustrates a non-limiting example of a single-ended TIA with alternating current (AC) coupling between a common source input stage and a source follower.
Figure 6:
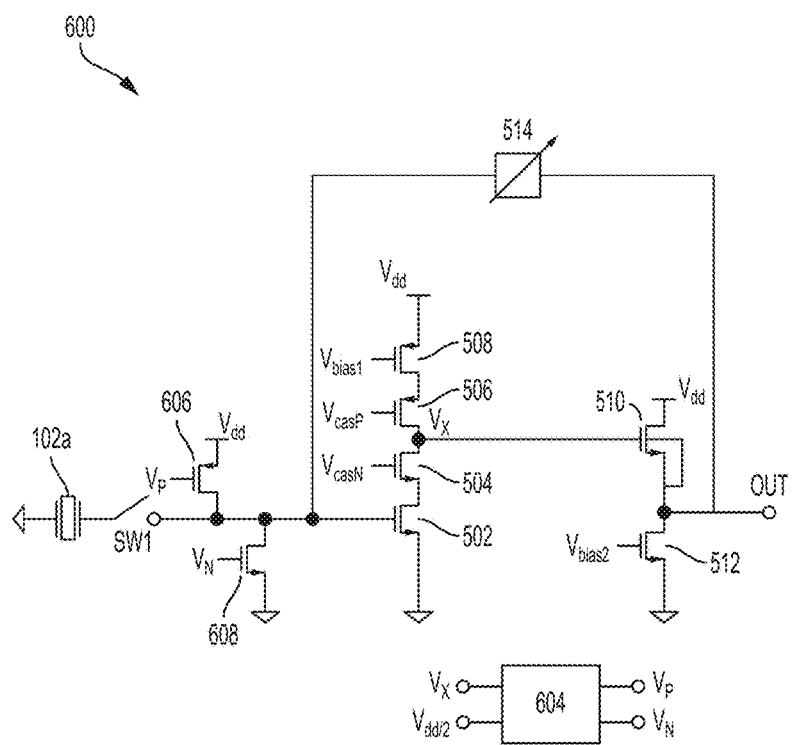
FIG. 6 illustrates a non-limiting example of a single-ended TIA with a bleeder circuit coupling a common source input stage to a source.
Figure 7:
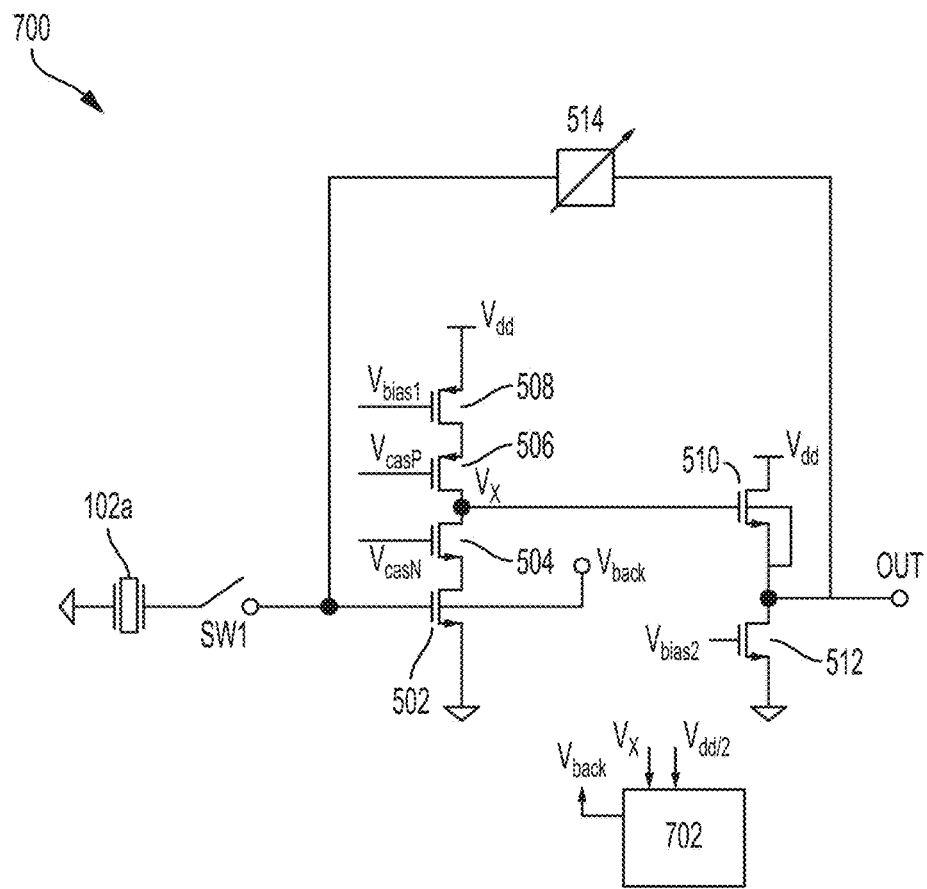
FIG. 7 illustrates a non-limiting example of a single-ended TIA having backgate voltage control of an input transistor.

While FIG. 2 illustrates an example of a single-ended TIA in accordance with various aspects of the present application, it should be appreciated that alternative implementations are possible. For example, while FIG. 2 illustrates the use of NMOS and PMOS transistors, different transistor technology may be used (e.g., bipolar junction transistor technology). Moreover, while FIG. 2 illustrates an NMOS common source and NMOS source follower, a PMOS common source and PMOS source follower could alternatively be implemented. Also, different circuit configurations may be used other than a common source followed by a source follower. FIGS. 5-7 illustrate various non-limiting alternative configurations.

FIG. 5 illustrates a non-limiting example of a single-ended TIA with alternating current (AC) coupling between a common source input stage and a source follower. The TIA 500 is connected to the ultrasonic transducer 102a, and includes transistors 502, 504, 506, 508, 510, and 512, switches SW1, SW2, SW3, and SW4, capacitor C1, and variable feedback impedance 514.

The TIA 500 includes a common source input stage. The common source input stage comprises transistors 502, 504, 506, and 508. Transistors 504 and 506 are configured in cascade, and receive cascade bias signals $V_{casN}$ and $V_{casP}$, respectively. Transistor 508 is a bias transistor configured to receive a bias voltage $V_{bias1}$.

The TIA 500 further comprises a source follower represented by transistor 510. A bias transistor 512 is coupled to the source follower and receives bias voltage $V_{bias2}$.

The TIA 500 includes AC coupling between the common source input stage and the source follower. The AC coupling is provided by switches SW2 and SW3, coupled to opposite plates of the capacitor C1. In some embodiments, the switches SW1, SW2, SW3, and SW4 are operated as follows. The switch SW1 may be a receive switch which is closed for the duration of a receive event, and opened when the ultrasound device is operating in a transmit mode. Prior to the beginning of a receive event, SW2 and SW4 are ON to pre-charge or reset the voltage across capacitor C1. During the receive period, and in at least some embodiments during the entire receive period encompassing the duration to receive at all target imaging depths, SW2 and SW4 are OFF and SW3 is ON, and capacitor C1 statically holds the charge from the pre-charge phase. The capacitor C1 is floating during this period and the voltage across the capacitor C1 during this period is such that Vx=Vdd/2.

The variable feedback impedance 514 may be of the same type as variable feedback impedance 214, described earlier, or any other suitable feedback impedance.

The TIA 500 may provide various benefits. For example, the source follower gate node (the node at the gate of transistor 510) does not limit the swing of the TIA. The capacitor C1 allows the gate node of the source follower to swing above Vdd. TIA 500 may also exhibit less noise than other two-stage operational amplifier designs.

FIG. 6 illustrates a variation on the single-ended TIA 500 of FIG. 5, lacking the AC coupling capacitor C1. The TIA 600 of FIG. 6 comprises the common source input stage and the source follower of FIG. 5, but lacks the capacitor C1 and instead includes a. current bleeding circuit (also referred to herein as a "bleeder circuit") including transistors 606 and 608, which may be considered current bleeding transistors. A feedback circuit 604 is provided to control the bleeder circuit. The feedback circuit 604 receives Vx and Vdd/2 as inputs and provides controls signals $V_P$ and $V_N$ to the bleeder circuit to control transistors 606 and 608 as shown in the configuration illustrated, the voltage Vx may be substantially centered at Vdd/2. It should be appreciated from FIG. 6 that an embodiment of the present application provides an ultrasound device including a signal receive circuitry chain comprising a single-ended TIA having a common source input stage coupled to a source follower by a bleeder circuit. Moreover, while FIG. 6 illustrates a bleeder circuit including two current bleeding transistors, an alternative is to use only one such transistor, 606 or 608. When only a positive or negative side current bleeding transistor is provided, the feedback circuit 604 may be simplified to provide only one of $V_P$ or $V_N$.

FIG. 7 illustrates a further non-limiting example of a single-ended TIA as may be used in an ultrasound device. In the example of FIG. 7, the single-ended TIA 700 exhibits backgate control of transistor 502. The TIA 700 does not use an AC coupling capacitor or a bleeder circuit. The TIA 700 includes the common source input stage and source follower of TIAs 500 and 600. Backgate control of the input common source NMOS transistor 502 is provided.

The backgate voltage of transistor 502 may be controlled by a positive programmable voltage to substantially maintain the backgate voltage Vback at a positive voltage between the supply rails, but not to exceed one diode turn-on voltage above 0V. The TIA 700 also includes a feedback circuit 702 configured to receive Vx and Vdd/2 and provide the voltage Vback. The construction of the backgate feedback control circuit 702 depends on whether positive or negative backgate control is being provided. When the TIA 700 is configured to provide positive backgate voltage. Vback may be maintained substantially above 0V in some embodiments. By contrast, when the TIA 700 is configured to provide negative backgate voltage, the circuit may include a negative power supply to provide the negative voltage or the feedback circuit 702 may include a charge pump to facilitate maintaining Vback below 0V. In such a situation, any suitable charge pump may be implemented. In some embodiments, an optional floating capacitor may be included to provide a voltage to the backgate, and in such embodiments the feedback circuit 702 may be disconnected during the receive period, with the backgate voltage Vback being provided by the floating capacitor.

It should be appreciated from FIG. 7 that an embodiment of the present application provides an ultrasound device including a signal receive circuitry chain comprising a single-ended TIA having backgate voltage control of an input transistor of the TIA.

In some embodiments, a signal receive circuitry chain of an ultrasound device may include a single-ended TIA followed by differential circuitry, such as a differential amplifier, averaging circuit, filter, or other circuitry. In such situations, the single-ended TIA may be combined with a replica circuit configured to generate a pseudo-differential input signal for downstream stages of the signal receive circuitry chain. In at least some seuch embodiments, the replica circuit may be substantially the same as the respective single-ended TIA but lacking a variable feedback impedance 514 and configured to produce a direct current (DC) output signal. In this manner, the TIA may produce a variable output signal corresponding to an output of the ultrasonic transducer and the replica circuit may generate a DC output, with those two outputs forming the pseudo-differential input signals to downstream differential circuitry in the signal receive circuitry chain. An exception is the circuit configuration having a bleeder circuit, for which the replica circuit still comprises the same variable feedback impedance as the single-ended TIA.

According to an aspect of the present application, an ultrasound signal receive chain includes a plurality of analog signal processing stages, in which at least two of the stages differ in the voltage swing they provide, In some embodiments, the stage prior to an ADC provides a different voltage swing than upstream (or preceding) analog processing stages. In some embodiments, the stage prior to the ADC provides a larger voltage swing than upstream (or preceding) stages. In this manner, power of the signal chain may be reduced, by providing a desired output voltage swing from the last stage prior to the conversion of the analog signal to a digital signal.

Figure 3:
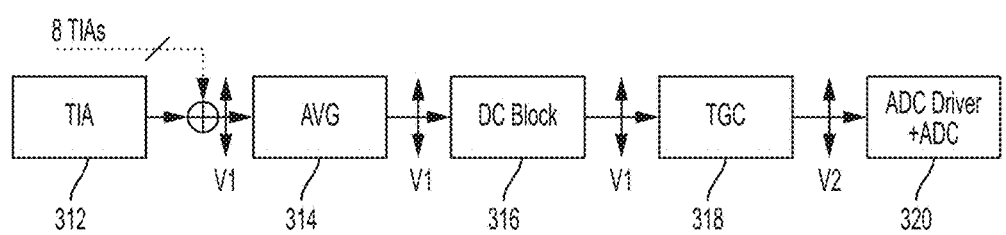
FIG. 3 illustrates an ultrasound signal receive circuitry chain including a single-ended TIA and a plurality of analog signal processing stages following the TIA, with voltage swings of the various stages illustrated, according to a non-limiting embodiment of the present application.

FIG. 3 illustrates an ultrasound signal receive circuitry chain including a single-ended TIA and a plurality of analog signal processing stages following the TIA, and may represent a generalized version of the corresponding signal processing stages of FIG. 1. The illustrated ultrasound receive circuitry chain includes eight TIAs 312, an averaging circuit 314, a DC block (or filter) stage 316, a time gain compensation stage 318, and a ADC driver and ADC stage 320. While eight TIAs 312 are shown, any suitable number may be included.

In the non-limiting example of FIG. 3, the illustrated analog signal processing stages provide the illustrated voltage swings. In particular, the TIAs 312, averaging circuit 314, and DC block stage 316 each provide an output voltage swing of V1, as indicated by the vertically indicated double-ended arrows. By contrast, the TGC stage 318 provides an output voltage swing of V2. In at least some embodiments, V2 may be greater than V1. For example, V2 may be between 1.5 and five times greater than V1, including any value and range within that range. As a non-limiting example, V1 may be between 0.2 Volts and 0.7 Volts (e.g., 0.5 Volts), while V2 may be between 1.5 and five times (e.g., two times, three times, or four times) greater than V1.

Operating the TIAs 312, averaging circuit 314, and DC block stage 316 with lower voltage swings V1 may reduce the power consumed by those stages. Low-swing operational amplifiers (op-amps) typically consume less power than operational amplifiers with larger swings. The desired output voltage swing for the signal chain may correspond to V2, and thus may be provided by the TGC stage 318, which in at least some embodiments is the analog signal processing stage immediately prior to the ADC driver and ADC. Thus, in some embodiments, all but the last stage of the analog signal processing chain have a lower output voltage swing than does the last stage, allowing for power savings in the stages having the lower output voltage swing.

In some embodiments, providing a larger voltage swing V2 with the TGC stage 318 may allow for providing lower gain from the TIAs 312, and thus conserving power with the TIAs 312. For example, the gain of the TIAs may be less than 100 dB in some embodiments, and the gain of the TGC may be between 5 dB and 30 dB in some embodiments. Other gains may may be implemented, as those listed are non-limiting examples.

While FIG. 3 illustrates multiple stages providing an output voltage swing V1, alternative embodiments provide configurations in which the stages preceding the TGC stage have non-uniform output voltage swings. For example, the TIAs 312, averaging circuit 314, and DC block stage 316 may provide different voltage swings than each other, but in at least some embodiments may all provide a lower output voltage swing than the TGC stage 318. Thus, in some embodiments, at least one analog processing stage preceding a time gain compensation stage provides a lower output voltage swing than the TGC stage.

Figure 4:
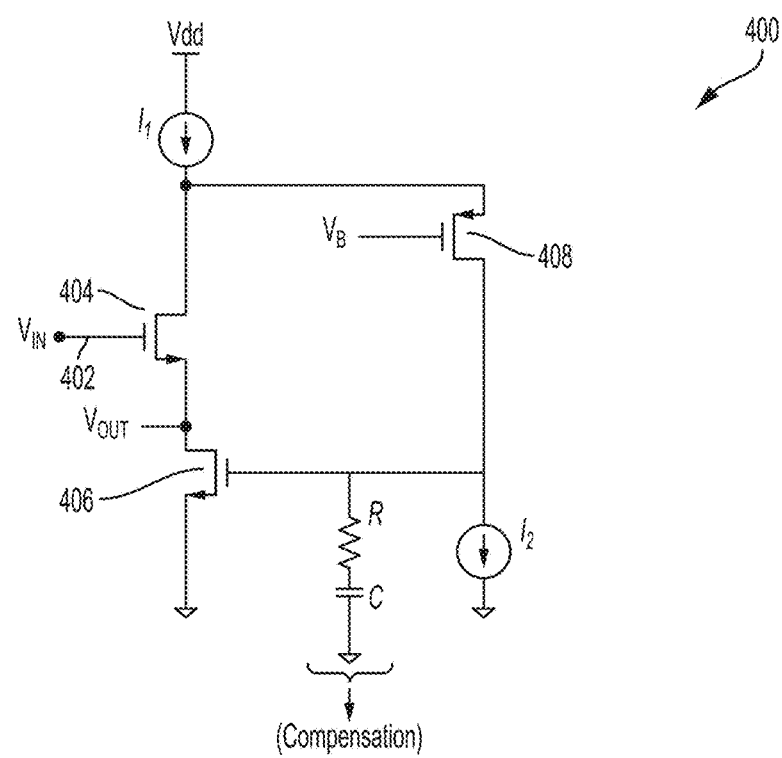
FIG. 4 illustrates an analog-to-digital converter (ADC) driver having a super source follower configuration, according to a non-limiting embodiment of the present application.

According to an aspect of the present application, an ultrasound signal receive circuitry chain includes an ADC and an ADC driver, and the ADC driver includes a super source follower. FIG. 4 illustrates an ADC driver having a folded cascode super source follower configuration, according to a non-limiting embodiment of the present application. The ADC driver 400 may be used as the ADC driver in the circuits of FIGS. 1 and 3, among other possible implementations.

The ADC driver 400 includes an input terminal 402 configured to receive an input signal, such as the output produced by a TGC stage, such as TGC stage 318 of FIG. 3. The input terminal 402 may correspond to the gate (or control terminal) of NMOS transistor 404. The output of the ADC driver 400 may be taken from the source of transistor 404. Transistor 404 is coupled to transistor 406.

The ADC driver 400 further comprises current sources $I_1$ and $I_2$, resistor R, capacitor C, and transistor 408. The resistor R and capacitor C may provide compensation to ensure sufficient phase margin for the loop and may have any suitable values for doing so. The cascode may be biased with a voltage $V_B$. The illustrated ADC driver structure may provide a relatively low output impedance by using feedback, while the folded cascode structure may allow for high output voltage swing. In this manner, the same output resistance associated with a source follower may be achieved with a relatively small bias current. While maintaining output voltage swing. Accordingly, the ADC driver may consume relatively little power compared to other configurations.

Using a super source follower as the ADC driver helps reduce the ADC driver power considerably in at least some embodiments. A super source follower reduces the output impedance by negative feedback rather than by increasing the current, but does so at the expense of supporting a smaller swing. The folded cascode super source follower according to the embodiments described herein exhibits the advantage of a super source follower in terms of lowering the power consumption needed to achieve a given output impedance, but also allows for a larger swing compared to a super source follower not having a folded cascade structure.

The ADC driver of FIG. 4 may be used with various types of ADCs. As an example, the illustrated ADC driver may be used with a successive approximation register (SAR) ADC. The combination of the illustrated ADC driver with a SAR ADC may provide low power operation coupled with high output voltage swing.

Having thus described several aspects and embodiments of the technology of this application, it is to be appreciated that various alterations, modifications, and improvements will readily occur to those of ordinary skill in the art. Such alterations, modifications, and improvements are intended to be within the spirit and scope of the technology described in the application. It is, therefore, to be understood that the foregoing embodiments are presented by way of example only and that, within the scope of the appended claims and equivalents thereto, inventive embodiments may be practiced otherwise than as specifically described.

As described, some aspects may be embodied as one or more methods. The acts performed as part of the method(s) may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The phrase "and/or," as used herein in the specification and in the claims, should be understood to mean "either or both" of the elements so conjoined, i.e., elements that are conjunctively present in sonie cases and disjunctively present in other cases.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements.

As used herein, the term "between" used in a numerical context is to be inclusive unless indicated otherwise. For example, "between A and B" includes A and B unless indicated otherwise.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

What is claimed is:

1. An ultrasound apparatus, comprising:
   an ultrasonic transducer; and
   a single-ended trans-impedance amplifier (TIA) having an input terminal coupled to the ultrasonic transducer and configured to receive and amplify an analog electrical signal from the ultrasonic transducer;
   wherein:
   the ultrasonic transducer is a first ultrasonic transducer and the single-ended TIA is a first single-ended TIA;
   the ultrasound apparatus comprises a plurality of ultrasonic transducers including the first ultrasonic transducer and a plurality of respective single-ended TIAs coupled to the respective ultrasonic transducers, the plurality of respective single-ended TIAs including the first single-ended TIA; and
   the ultrasound apparatus further comprises:
   an averaging circuit having an input coupled to the plurality of respective single-ended TIAs;
   a filter and a time gain compensation (TGC) circuit, the filter being coupled electrically between the averaging circuit and the TGC circuit;
   an analog-to-digital converter (ADC) coupled to an output terminal of the TGC circuit; and
   an ADC driver coupled to the ADC and configured to drive the ADC, the ADC driver comprising a folded cascode super source follower.

2. The ultrasound apparatus of claim 1, further comprising a switch coupled between the first ultrasonic transducer and the input terminal of the first single-ended TIA.

3. The ultrasound apparatus of claim 1, wherein the plurality of respective single-ended TIAs are configured to exhibit a first voltage swing, and wherein the TGC circuit is configured to exhibit a second voltage swing greater than the first voltage swing.

4. The ultrasound apparatus of claim 3, wherein the second voltage swign is between 1.5 and five times greater than the first voltage swing.

5. The ultrasound apparatus of claim 3, wherein the averaging circuit and filter are configured to exhibit a voltage swing less than the second voltage swing.

6. The ultrasound apparatus of claim 5, wherein the averaging circuit and filter are configured to exhibit the first voltage swing.

7. The ultrasound apparatus of claim 3, wherein the plurality of ultrasonic transducers, plurality of respective single-ended TIAs, filter, and TGC circuit are formed on a single substrate.

8. The ultrasound apparatus of claim 7, wherein the plurality of ultrasonic transducers are capacitive micromachined ultrasonic transducers (CMUTs).

9. The ultrasound apparatus of claim 1, wherein the first single-ended TIA comprises a common source circuit coupled to a source follower.

10. An ultrasound circuit, comprising:
an ultrasonic transducer; and
a plurality of analog processing stages coupled to an output of the ultrasonic transducer and including one analog processing stage configured to exhibit a greater voltage swing than other analog processing stages of the plurality of analog processing stages;
wherein the one analog processing stage configured to exhibit the greater voltage swing is a time gain compensation (TGC) circuit.

11. The ultrasound circuit of claim 10, wherein the TGC circuit is the last analog processing stage before an analog-to-digital converter (ADC).

12. The ultrasound circuit of claim 10, wherein the one analog processing stage configured to exhibit a greater voltage swing is the last analog processing stage before an analog-to-digital converter (ADC).

13. The ultrasound circuit of claim 10, wherein the plurality of analog processing stages comprises a single-ended trans-impedance amplifier.

14. The ultrasound circuit of claim 10, further comprising an analog-to-digital converter (ADC) and an ADC driver coupled to a last analog processing stage of the plurality of analog processing stages, the ADC driver comprising a folded cascode super source follower.

15. An ultrasound circuit, comprising:
an ultrasonic transducer;
an amplifier having an input terminal coupled to the ultrasonic transducer; and
a time gain compensation (TGC) circuit, wherein the amplifier is electrically coupled between the ultrasonic transducer and the TGC circuit, and
wherein the amplifier is configured to exhibit a first voltage swing and the TGC circuit is configured to exhibit a second voltage swing greater than the first voltage swing.

16. The ultrasound circuit of claim 15, wherein the amplifier is a single-ended trans-impedance amplifier (TIA).

17. The ultrasound circuit of claim 16, wherein the single-ended TIA comprises a common source circuit coupled to a source follower.

18. The ultrasound circuit of claim 15, further comprising an analog-to-digital converter (ADC) driver coupled electrically downstream of the TGC, the ADC driver comprising a folded cascode super source follower.

* * * * *